(12) United States Patent
Diao et al.

(10) Patent No.: US 10,869,735 B2
(45) Date of Patent: Dec. 22, 2020

(54) MEDICAL INSTRUMENT WITH AN INTEGRATED OPTICAL FIBER

(71) Applicant: Novartis AG, Basel (CH)

(72) Inventors: Chenguang Diao, Irvine, CA (US); Mark Harrison Farley, Laguna Hills, CA (US); Brian William McDonell, Irvine, CA (US); Alireza Mirsepassi, Irvine, CA (US); Michael J. Papac, North Tustin, CA (US); Kambiz Parto, Laguna Niguel, CA (US); Ronald T. Smith, Irvine, CA (US); Barry L. Wheatley, Oceanside, CA (US)

(73) Assignee: Alcon Inc., Fribourg (CH)

( * ) Notice: Subject to any disclaimer, the term of this patent is extended or adjusted under 35 U.S.C. 154(b) by 141 days.

(21) Appl. No.: 15/805,519

(22) Filed: Nov. 7, 2017

(65) Prior Publication Data
US 2018/0132963 A1 May 17, 2018

Related U.S. Application Data

(60) Provisional application No. 62/423,499, filed on Nov. 17, 2016.

(51) Int. Cl.
*A61B 90/30* (2016.01)
*A61B 18/00* (2006.01)
(Continued)

(52) U.S. Cl.
CPC .............. *A61B 90/30* (2016.02); *A61B 18/00* (2013.01); *A61F 9/00736* (2013.01);
(Continued)

(58) Field of Classification Search
CPC ........... A61B 1/06; A61B 1/0661; A61B 1/07; A61B 90/30; A61B 2090/306
(Continued)

(56) References Cited

U.S. PATENT DOCUMENTS

| 4,566,438 A | * | 1/1986 | Liese | ............... A61B 5/6848 600/129 |
| 5,201,730 A | | 4/1993 | Easley et al. | |

(Continued)

FOREIGN PATENT DOCUMENTS

JP    2005532139 A    10/2005

OTHER PUBLICATIONS

Fisher et al., Inexpensive Illuminated Vitrectomy Cutter, The Journal of Retinal and Vitreous Diseases, Dec. 2003, vol. 23, Issue 6, p. 891.

(Continued)

*Primary Examiner* — Julianna N Harvey
*Assistant Examiner* — Christina Negrellirodriguez

(57) ABSTRACT

Provided herein is an illuminated microsurgical instrument system and an illuminated microsurgical instrument. In one implementation, the system includes a microsurgical instrument having a distally projecting tubular member arranged to perform a medical procedure at an interventional site. The tubular member has a distal tip and an outer surface, the outer surface having a flat surface formed therein. The instrument includes a sheath member surrounding a portion of the tubular member and extending toward the distal tip of the tubular member and an optical fiber extending along a length of the flat surface between the tubular member and the sheath member. The instrument may further include a slack chamber, collar structure, and fiber guard member to support and guide the optical fiber to the distal tip.

18 Claims, 9 Drawing Sheets

(51) Int. Cl.
*A61F 9/007* (2006.01)
*A61B 17/00* (2006.01)

(52) U.S. Cl.
CPC .............. *A61F 9/00763* (2013.01); *A61B 2017/00345* (2013.01); *A61B 2090/306* (2016.02)

(58) Field of Classification Search
USPC ....... 600/160, 161, 164, 171, 174, 175, 182, 600/249
See application file for complete search history.

(56) References Cited

U.S. PATENT DOCUMENTS

| | | | |
|---|---|---|---|
| 5,275,593 | A | 1/1994 | Easley et al. |
| 5,591,160 | A | 1/1997 | Reynard |
| 5,651,783 | A | 7/1997 | Reynard |
| 7,783,346 | B2 | 8/2010 | Smith et al. |
| 8,900,139 | B2 | 12/2014 | Yadlowsky et al. |
| 8,968,347 | B2 | 3/2015 | McCollam |
| 9,055,885 | B2 | 6/2015 | Horvath et al. |
| 9,089,364 | B2 | 7/2015 | Bhadri et al. |
| 9,364,982 | B2 | 6/2016 | Schaller |
| 9,402,643 | B2 | 8/2016 | Auld et al. |
| 9,561,085 | B2 | 2/2017 | Yadlowsky et al. |
| 9,839,749 | B2 | 12/2017 | Johnson et al. |
| 9,956,053 | B2 | 5/2018 | Diao et al. |
| 10,016,248 | B2 | 7/2018 | Mirsepassi et al. |
| 10,039,669 | B2 | 8/2018 | Heeren |
| 2007/0118014 | A1* | 5/2007 | Fuerst ................ A61B 1/00167 600/138 |
| 2009/0161384 | A1 | 6/2009 | Smith |
| 2010/0004642 | A1 | 1/2010 | Lumpkin |
| 2010/0191177 | A1 | 7/2010 | Chang et al. |
| 2012/0283523 | A1 | 11/2012 | Yadlowsky et al. |
| 2014/0121469 | A1 | 5/2014 | Meckel et al. |
| 2016/0113722 | A1 | 4/2016 | Heeren |
| 2017/0014023 | A1 | 1/2017 | Kern |
| 2017/0014267 | A1 | 1/2017 | Kern et al. |
| 2017/0119491 | A1 | 5/2017 | Mirsepassi et al. |
| 2017/0165114 | A1 | 6/2017 | Hallen et al. |
| 2018/0055596 | A1 | 3/2018 | Johnson |
| 2018/0133057 | A1 | 5/2018 | Diao et al. |
| 2018/0168768 | A1 | 6/2018 | Mirsepassi et al. |
| 2018/0168861 | A1 | 6/2018 | Mirsepassi et al. |
| 2018/0338776 | A1 | 11/2018 | Farley et al. |
| 2018/0338859 | A1 | 11/2018 | Mirsepassi et al. |
| 2018/0338860 | A1 | 11/2018 | Farley |

OTHER PUBLICATIONS

Chalam, et al., Illuminated Curved Vitrectomy Probe for Vitreoretinal Surgery, Ophthalmic Surgery, Lasers and Imaging, Nov./Dec. 2007—vol. 38 Â—Issue 6: 525-526.

* cited by examiner

MEDICAL INSTRUMENT WITH AN INTEGRATED OPTICAL FIBER

This application claims the benefit of priority of U.S. Provisional Patent Application Ser. No. 62/423,499 titled "Medical Instrument with an Integrated Optical Fiber", filed on Nov. 17, 2016, whose inventors are Chenguang Diao, Mark Harrison Farley, Brian William McDonell, Alireza Mirsepassi, Michael J. Papac, Kambiz Parto, Ronald T. Smith and Barry L. Wheatley, which is hereby incorporated by reference in its entirety as though fully and completely set forth herein.

TECHNICAL FIELD

The present disclosure is directed to systems and instruments for use in medical procedures, and more particularly, to methods and systems involving a need for an optical fiber to be inserted within a body cavity.

BACKGROUND

Medical procedures are often performed within significantly limited confines of a particular body structure or cavity, such as within the posterior chamber of the human eye. For example, vitreo-retinal procedures are commonly performed to treat many serious conditions of the posterior segment of the eye. In particular, vitreo-retinal procedures may treat conditions such as age-related macular degeneration (AMD), diabetic retinopathy and diabetic vitreous hemorrhage, macular hole, retinal detachment, epiretinal membrane, cytomegalovirus (CMV) retinitis, and many other ophthalmic conditions.

A surgeon performs vitreo-retinal procedures with a microscope and special lenses designed to provide a clear image of the posterior segment. Several tiny incisions just a millimeter or so in diameter are made on the sclera at the pars plana. The surgeon inserts microsurgical instruments through the incisions, such as a light source to illuminate inside the eye, an infusion line to maintain the eye's shape during surgery, and other instruments to cut and remove the vitreous body. A separate incision may be provided for each microsurgical instrument when using multiple instruments simultaneously.

During such procedures, proper illumination of the inside of the eye is important. Typically, an optical fiber is inserted into one of the incisions in the eye to provide the illumination. A light source, such as a halogen tungsten lamp or high pressure arc lamp (metal-halides, Xenon), may be used to produce the light carried by the optical fiber into the eye. The light passes through several optical elements (typically lenses, mirrors, and attenuators) and is transmitted to the optical fiber that carries the light into the eye.

In such procedures, incisions are typically only made large enough to accommodate the size of the microsurgical instrument being inserted into the interior of the eye. Efforts to minimize the incision size generally involve reducing the size of the microsurgical instrument. However, a reduction in size can result in a reduction in instrument strength or rigidity. Depending on the size of the microsurgical instrument employed, the incision may be small enough to render a resulting wound substantially self-healing, thereby eliminating the need to employ additional procedures to close the incision, such as sutures. Also, reducing the number of incisions may be accomplished by integrating various microsurgical instruments. For example, the optical fiber may be incorporated into the working end of a microsurgical instrument. Unfortunately, at least some prior attempts at integrating optical fibers with microsurgical instruments have resulted in a decrease in illuminating efficiency or in other visualization problems that otherwise adversely effected the distribution of light emitted from the optical fibers.

SUMMARY

The present disclosure is directed to exemplary illuminated microsurgical instruments.

Exemplary surgical systems are provided herein. One general aspect includes an illuminated microsurgical instrument system that may include a microsurgical instrument having a distally projecting tubular member arranged to perform a medical procedure at an interventional site. The tubular member may have a distal tip and an outer surface, the outer surface having a flat surface formed therein. The instrument may include a sheath member surrounding a portion of the tubular member and extending toward the distal tip of the tubular member and an optical fiber extending along a length of the flat surface between the tubular member and the sheath member.

Another general aspect includes another illuminated microsurgical instrument system. The system may include a microsurgical instrument having a tubular member arranged to perform a medical procedure at an interventional site, the tubular member may have a distal tip and an outer cylindrical surface. The instrument may include a sheath member surrounding a portion of the tubular member and extending toward the distal tip of the tubular member and an optical fiber extending along a length of the tubular member between the outer cylindrical surface and an inner surface of the sheath member. The tip of the optical fiber may be recessed or set back proximally from a distal edge of the tubular member.

Exemplary vitrectomy probes are provided herein. One general aspect includes an illuminated medical probe, which may include a handpiece housing configured to be held in a human hand. The handpiece housing may include a distal end arranged to receive an optical fiber coupled to an illumination source and a proximal end coupled to an elongate tubular member. The illuminated medical probe may also include an optical fiber slack chamber disposed between the distal end and the proximal end. Additionally, the illuminated medical probe may have an optical fiber extending within the optical fiber slack chamber and extending along a portion of the elongate tubular member. A distal region of the optical fiber may be secured at a distal end thereof to the elongate tubular member. The optical fiber may have a slack portion including a bend disposed within the optical fiber slack chamber.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the accompanying drawings and the following detailed description.

BRIEF DESCRIPTION OF THE DRAWINGS

The accompanying drawings illustrate implementations of the devices and methods disclosed herein and together with the description, serve to explain the principles of the present disclosure.

Figure 1:
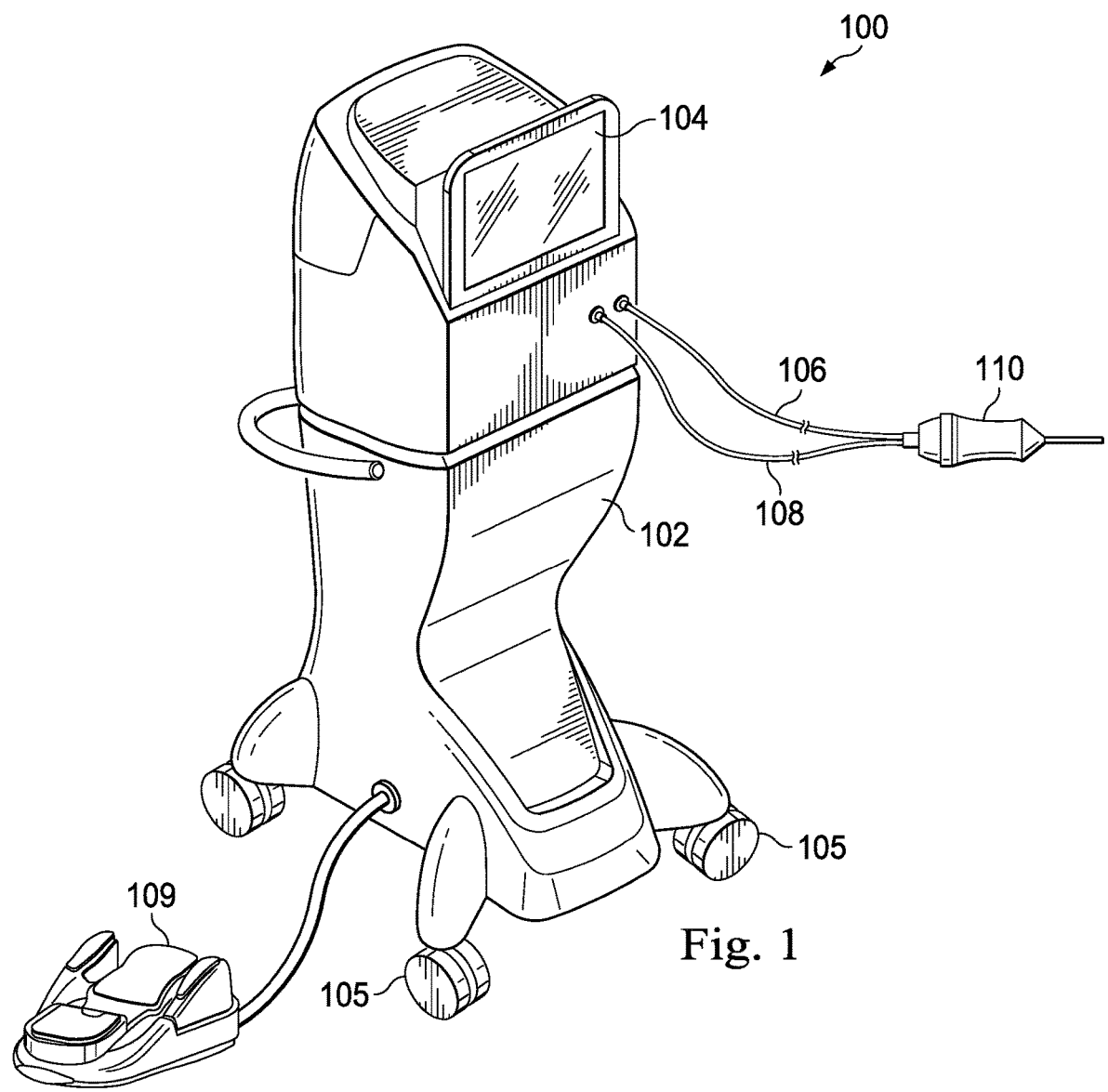
FIG. 1 illustrates a perspective view of an exemplary surgical system, according to an implementation consistent with the principles of the present disclosure.

The accompanying drawings may be better understood by reference to the following detailed description.

DETAILED DESCRIPTION

For the purposes of promoting an understanding of the principles of the present disclosure, reference will now be made to the implementations illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one implementation may be combined with the features, components, and/or steps described with respect to other implementations of the present disclosure. For simplicity, in some instances the same reference numbers are used throughout the drawings to refer to the same or like parts.

The present disclosure is broadly directed to systems and instruments for providing an optical fiber within a body cavity during an operation performed therein without requiring a separate incision to be made. More particularly, some aspects of the present disclosure at directed to systems and instruments for providing for illumination through an optical fiber positioned within the body cavity. In some examples, the illumination is provided through an optical fiber extending along a length of another surgical instrument or tool within the body cavity. For example, a vitrectomy procedure may be performed to remove vitreous from the eye of a patient using a vitrectomy probe and introduced into the eye to position a vitrectomy needle at an interventional site. Rather than form two incisions in the eye of the patient, the optical fiber may be positioned along a portion of the vitrectomy needle. The optical fiber may have a distal tip through which light is introduced or emitted into the posterior chamber of the eye, when the distal tip of the vitrectomy probe is positioned within the eye. The removal of the vitreous may be of particular importance, because residual vitreous can cause post-operative retinal tearing, retinal detachment, etc.

The clear vitreous may be visualized due to light scattering off the vitreous fibers contained within it. The lighting may be directed proximate the cutting portion of the vitrectomy probe in order to better visualize the vitreous being cut. Depending on the implementation, the optical fiber may be secured at least partially to a vitrectomy needle by a sheath that also protects the optical fiber. Thus, implementations of the present disclosure provide for improved illumination for inner-cavity procedures, such as vitrectomy procedures, while minimizing the number of incisions required to be made to permit entry to the cavity. The illumination provided by implementations of the present disclosure may result in high irradiance at the surgical site, e.g., at the port of the vitrectomy needle. This may provide for a high signal to noise ratio or contrast to facilitate visualization of the fibers in the vitreous. While specific examples of implementations are provided herein that are directed to vitrectomy procedures and devices, the principles of the present disclosure extend beyond vitrectomy instruments and procedures.

FIG. 1 illustrates a surgical system 100, according to an exemplary implementation. The surgical system 100 includes a base housing or console 102 and an associated display screen 104. In the implementations of the surgical system 100 that are directed to vitrectomy procedures, the display screen 104 may show data relating to system operation and performance during such vitrectomy surgical procedures. In an implementation, the console 102 may be mobile, for example including casters or wheels 105 to facilitate movement as necessary. In an alternative implementation, the console 102 may not include wheels 105.

The console 102 may be referred to as a "base housing" and may include a plurality of subsystems that cooperate to enable a surgeon to perform a variety of medical procedures, such as ophthalmic surgical procedures. A microsurgical, or simply "surgical," instrument 110, which may be implemented as a handpiece, may attach to the console 102 and may form a part of the surgical system 100. The surgical instrument 110 may be a vitrectomy probe, in some implementations. Additionally, some implementations of the instrument 110 may include non-surgical medical instruments, such as diagnostic instruments, imaging instruments, or therapeutic instruments. As illustrated in FIG. 1, the surgical instrument 110 is an illuminated vitrectomy probe that may form part of a vitrectomy subsystem as described herein.

The surgical instrument 110 may be coupled to the console 102 by one or more conduits. In the depicted implementation, the surgical instrument 110 is coupled to the console 102 by a first conduit 106 and a second conduit 108. The conduits 106 and 108 may provide the surgical instrument 110 with access to multiple subsystems of the console 102. For example, the first conduit 106 may contain an optical fiber coupled to or forming part of a fiber subsystem within the console 102, while the second conduit 108 may couple the surgical instrument 110 to or may form a part of a fluidics subsystem.

To facilitate operator control of the surgical system 100, the surgical instrument 110 itself may include one or more control elements, such as buttons or dials. Additionally, a footpedal 109 may include control elements that can be activated, deactivated, or varied by the operator's foot. Moreover, the display screen 104 may be a touchscreen having controls displayed thereon that can be manually activated by the operator. Other mechanisms such as voice control, a keyboard, a mouse, etc., may be provided in various implementations of the surgical system 100 to facilitate control of various subsystems, such as a fiber subsystem to facilitate visualization, diagnosis, or treatment at a distal region of the surgical instrument 110.

Figure 2:
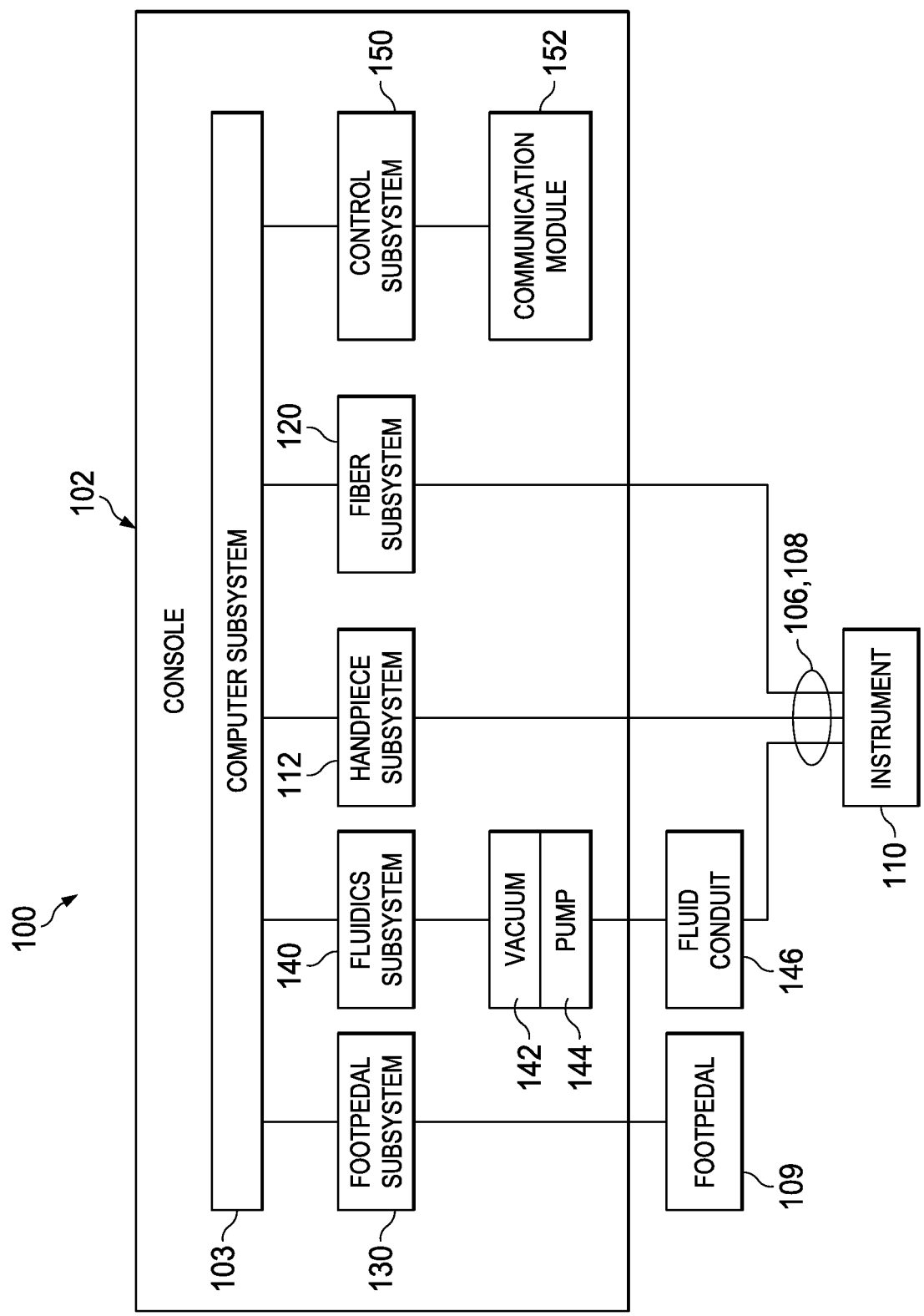
FIG. 2 is an illustration of an exemplary block diagram of the surgical system of FIG. 1, according to an aspect consistent with the principles of the present disclosure.

FIG. 2 is a block diagram of the surgical system 100 including the console 102 and several relating subsystems thereof. As illustrated, console 102 includes a computer subsystem 103, the display screen 104 (FIG. 1), and a number of subsystems that are used together to perform ocular surgical procedures, such as emulsification or vitrectomy surgical procedures, for example. The computer subsystem 103 may include one or more processing devices, such as a central processing unit or central processor, and an information or data storage system. The data storage system may include one or more types of memory, such as RAM (Random-access memory), ROM (read-only memory), flash memory, a disk-based hard drive, and/or a solid-state hard drive. The processing devices and storage system may communicate over a bus, which may also permit communication with and between one or more of the plurality of subsystems of the surgical system 100.

The subsystems in the exemplary implementation of FIG. 2 may include a footpedal subsystem 130 including, for example, for facilitating control via the footpedal 109 of FIG. 1. The depicted surgical system 100 further includes a fluidics subsystem 140, which may include an aspiration vacuum 142 and an irrigation pump 144 that connect to a fluid conduit 146. The surgical system 100 includes a handpiece subsystem 112 to facilitate operation and control of the surgical instrument 110. For example, the handpiece subsystem 112 may receive control signals from the surgical instrument 110 to turn on or off an illumination source coupled to the surgical instrument 110.

Implementations of an included fiber subsystem 120 may provide an illumination source. Other implementations of the fiber subsystem 120 may provide laser light for ablation, may be used in imaging through the optical fiber, or other functions. The fiber subsystem 120, which may be an illumination subsystem, may be coupled to the surgical instrument 110 by an optical fiber, extending within one of the first and second conduits 106 and 108. The fiber subsystem 120 may include or be referred to as an illumination source or light source, although the source may be one component of several components of the fiber subsystem 120. Implementations of the fiber subsystem 120 may further include sensors, lenses, filters, and other optical devices.

The surgical system 100 further includes a control subsystem 150 including a communication module 152. The control subsystem 150 may facilitate communication between the subsystems included in the surgical system 100. For example, an operator may provide an input via the footpedal 109. The input may be interpreted or encoded by the footpedal subsystem 130 as a control signal to vary, for example, an intensity of illumination provided to the surgical instrument 110. The footpedal subsystem 130 may communicate the control signal to the control subsystem 150, which may interact with a fiber subsystem 120 to alter a characteristic of the illumination provided by the subsystem 120 or to turn the illumination on or off. In some implementations, the surgical instrument 110 may, additionally or alternatively, be used to control illumination status or intensity. For example, the surgical instrument 110 may include a dimmer switch or other control mechanism to receive input from an operator to adjust the illumination.

These subsystems and others may be included additionally or alternatively in other implementations. To optimize performance of the different subsystems during surgery, the operating parameters differ according to, for example, the particular procedure being performed, the different stages of the procedure, the surgeon's personal preferences, whether the procedure is being performed in the anterior or posterior portion of the patient's eye, and so on.

The different subsystems in the console 102 comprise control circuits for the operation and control of the respective microsurgical instruments or instrument components. The computer subsystem 103 and the control subsystem 150 may govern and dynamically redefine the interactions and relationships between the different subsystems to properly perform an ocular surgical procedure and to properly communicate information to the operator of the surgical system 100 through the display 104 and/or through a coupled microscope or wearable computing device.

As shown in FIG. 2, the surgical instrument 110 may be coupled to various subsystems within the surgical system 100. As depicted, the surgical instrument 110 is connected to the handpiece subsystem 112, the fiber subsystem 120, and the fluidic subsystem 140 via the conduits 106 and/or 108 as shown in FIG. 1.

Using the input devices, a surgeon, scientist, or other user may select or adjust parameters that affect the relationships between the different subsystems of the console 102 and that affect the performance of the surgical instrument 110 and/or additional instruments connected to the console 102. For example, a surgeon may increase or decrease an intensity of light provided by the fiber subsystem 120. Additionally, a surgeon may change one or more parameters for the operation of the surgical instrument 110, such as an aspiration/suction parameter or an oscillation parameter of the vitreous cutting mechanism included in the surgical instrument 110. Accordingly, based on a user input, a user may change or adjust the relationships from those that were coded into the console by the system programmers.

Because the surgical instrument 110 is configured to receive light from the fiber subsystem 120, the surgeon may be able to visualize aspects of the surgical operations performed by or near by the distal tip of the surgical instrument 110, without requiring multiple incisions and without requiring the manipulation and handling of two or more separate devices within the small confines of the eye or in another cavity or area of the patient.

Figure 3:
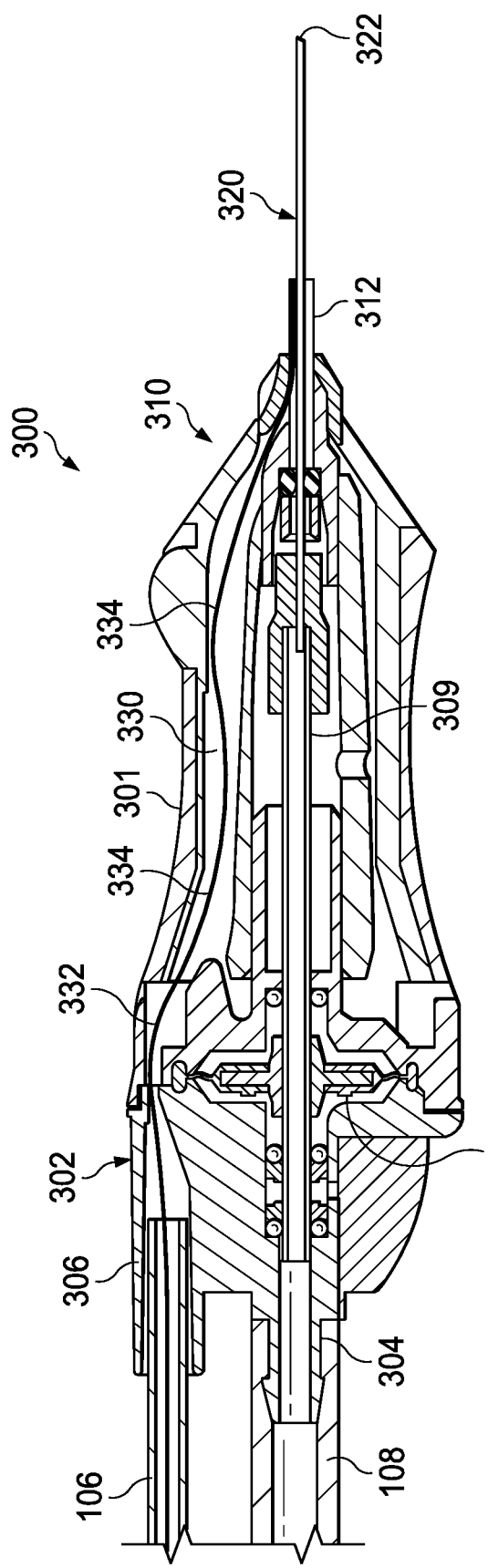
FIG. 3 is a cross-sectional illustration of an exemplary surgical instrument, according to aspects of the present disclosure.

FIG. 3 shows a partial cross-sectional illustration of an exemplary vitrectomy probe 300 that may correspond to the surgical instrument 110 shown in FIGS. 1 and 2. In this example, the probe 300 may be a pneumatically-driven vitrectomy probe configured to be held in the hand of a surgeon during use. The probe 300 includes a handpiece housing 301 having a proximal end 302 and a distal end 310. Some implementations of the probe 300 operate by receiving pneumatic pressure via the second conduit 108 of FIG. 1, which may be coupled to a protruding coupler 304 at the proximal end 302. The coupler 304 may attach the proximal end 302 of the probe 300 to the second conduit 108 by a barb, an adhesive, or other coupling means. The proximal end 302 further includes an additional coupler 306 that is configured to receive or couple to the first conduit 106 of FIG. 1.

In this implementation, the second conduit 108 provides an activation energy source to provide an oscillation energy to components of the probe 300. As illustrated, a pneumatic source may form a part of the fluidics subsystem 140 of FIG. 2 and may be coupled to an oscillation motor, shown here as a diaphragm 308. In some embodiments, the oscillation motion may be provided by an oscillating electric motor or other non-pneumatic activation means. Further, the conduit 108 may be coupled to an aspiration source to enable aspiration of material through the probe 300. By causing the diaphragm 308 to oscillate, a drive member 309 may also be caused to vibrate or oscillate. The drive member 309 may extend between the proximal end 302 and the distal end 310. The drive member 309 may be an elongate tubular member having a lumen extending therethrough such that material may be aspirated to the console 102 or material may be pumped through the drive member 309 to the distal end 310 of the probe 300.

As depicted in FIG. 3, the distal end 310 of the handpiece housing 301 includes or supports a collar structure 312 that provides a degree of rigidity and support to a vitrectomy needle 320. The vitrectomy needle 320 may include inner and outer components that may be used for cutting vitreous proximate a distal tip 322 of needle 320 during vitrectomy procedures as is described herein and in further detail.

The handpiece housing 301 includes a chamber 330 that extends from the proximal end 302 to the distal end 310. The chamber 330 may be referred to herein as an optical fiber slack chamber 330. A length of an optical fiber 332 extends within the slack chamber 330. For example, the optical fiber 332 may extend from the fiber subsystem 120, through the first conduit 106, through the optical fiber slack chamber 330, through the collar structure 312, and along the vitrectomy needle 320. The fiber may terminate anywhere along the needle 320, such as at or near the distal tip 322 thereof or closer to the distal end 310 of the handpiece housing 301. The optical fiber 332 may be affixed to the needle 320 at a distal region of the fiber 332, which may provide a proximal region of the needle over which the optical fiber 332 is permitted to axially displace independently of the needle 320, in some implementations. In some other implementations (e.g., as seen in FIGS. 4A-6B), the optical fiber 332 may be affixed to the sheath 340. When the needle 320 flexes during use in a medical procedure, the portion of the fiber 332 extending along the needle 320 may relatively, axially displace according to the direction of bending of the needle 320. To prevent strain on the optical fiber 332, the collar structure 312 may include one or more passages with guiding surfaces to permit independent elongate displacement of the optical fiber 332 along a proximal region of the needle 320 within the space between the tubular member 342 and sheath 340, and to permit slideable transition of the optical fiber 332 through a straight, offset or curved path between the needle 320 and the slack chamber 330. The slack chamber 330 may include sufficient space to accommodate slack optical fiber in one or more fiber bends 334. The fiber bends 334 may have a radius of curvature sufficiently large to avoid affecting the illumination passing through the optical fiber 332, while still providing for an amount of slack fiber to be contained within the optical fiber slack chamber 330. The optical fiber 332 may have a portion fixed within the proximal portion of the slack chamber 330 or the distal end of the handpiece housing 301. Accordingly, the amount of slack fiber may accommodate flexing of the vitrectomy needle 320. Some implementations of the probe 300 may include an optical fiber slack chamber in the coupled conduit 106 in addition to or as an alternative to the slack chamber 330 included in the handpiece housing 301.

Figure 4A:
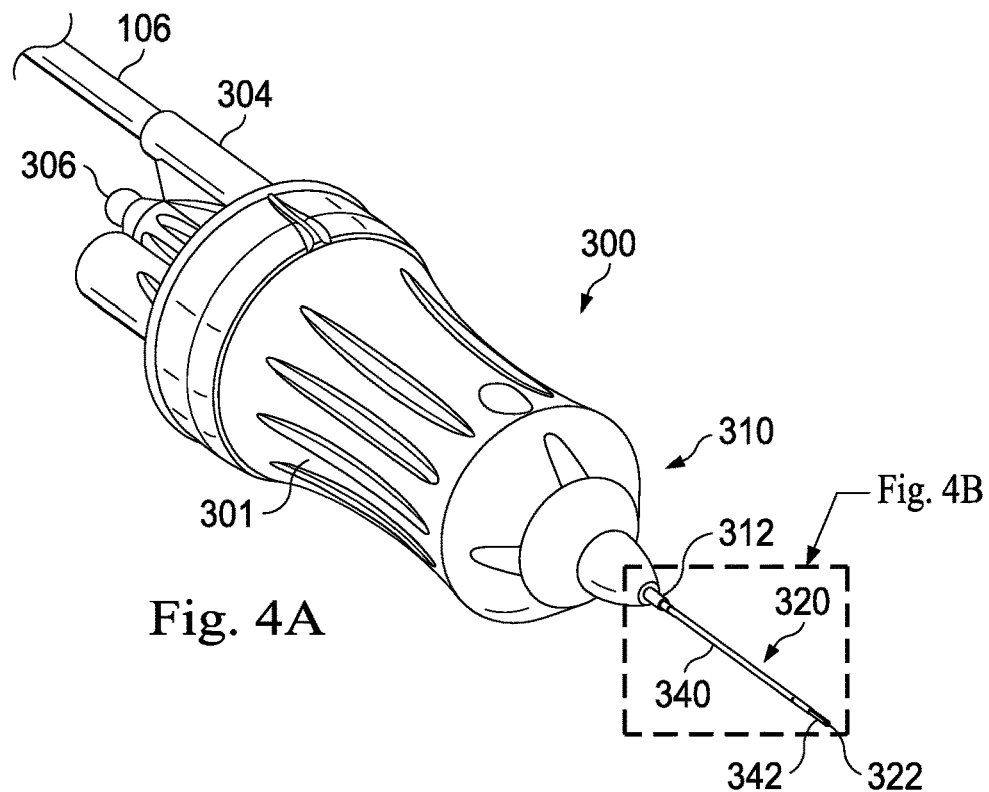
FIG. 4A is a perspective view of the surgical instrument of FIG. 3, according to aspects of the present disclosure.
Figure 4B:
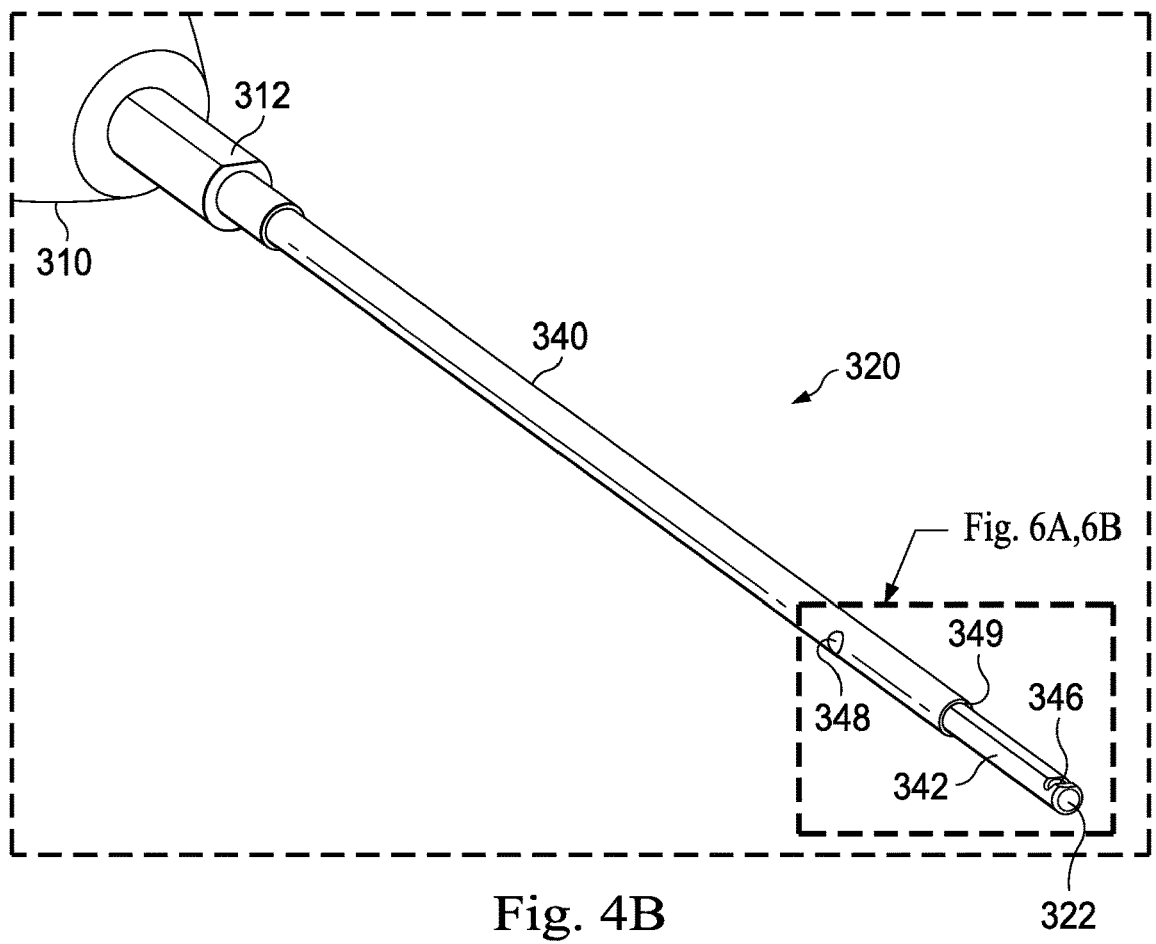
FIG. 4B is a detailed perspective view of a portion of the distal end of the surgical instrument included in FIG. 4A, according to aspects of the present disclosure.

FIGS. 4A and 4B provide perspective views of the probe 300 of FIG. 3. Both of these figures depict an implementation of the needle 320. As shown in FIG. 4A, the needle 320 includes a sheath 340 extending along an outer surface of an elongate tubular member 342. The elongate tubular member 342 extends beyond a distal edge 349 (shown in more detail in FIG. 5A) of the sheath 340. The distal tip 322 may be the distal tip of the elongate tubular member 342. FIG. 4B is a more detailed view of the needle 320 depicted in FIG. 4A. FIG. 4B further illustrates that the elongate tubular member 342 can include an opening or port 346, into which vitreous may be aspirated and cut during a vitrectomy procedure. FIG. 4B also depicts an opening 348 in the sheath 340. The opening 348 may provide a window through which a liquid or gel sealant material may be introduced to seal off any small gaps that are present between the inner surface of the sheath 340 and the outer surface of the elongate tubular member 342. In some implementations, multiple openings may be provided in the sheath 340 to provide for the introduction of a sealant. The opening 348 may also be provided in or proximate to the collar structure 312 at the distal end 310 of the housing 301. In some implementations, the sealant is a gel that can be injected through the opening 348. The gel may be cured after injection to further ensure a proper seal between the sheath 340 and the elongate tubular member 342. Affixing the optical fiber 332 to the sheath 340 may result in passive alignment of the optical fiber 332 relative to the sheath 340. The passive alignment may minimize glare and reduce the assembly cost.

Figure 5A:
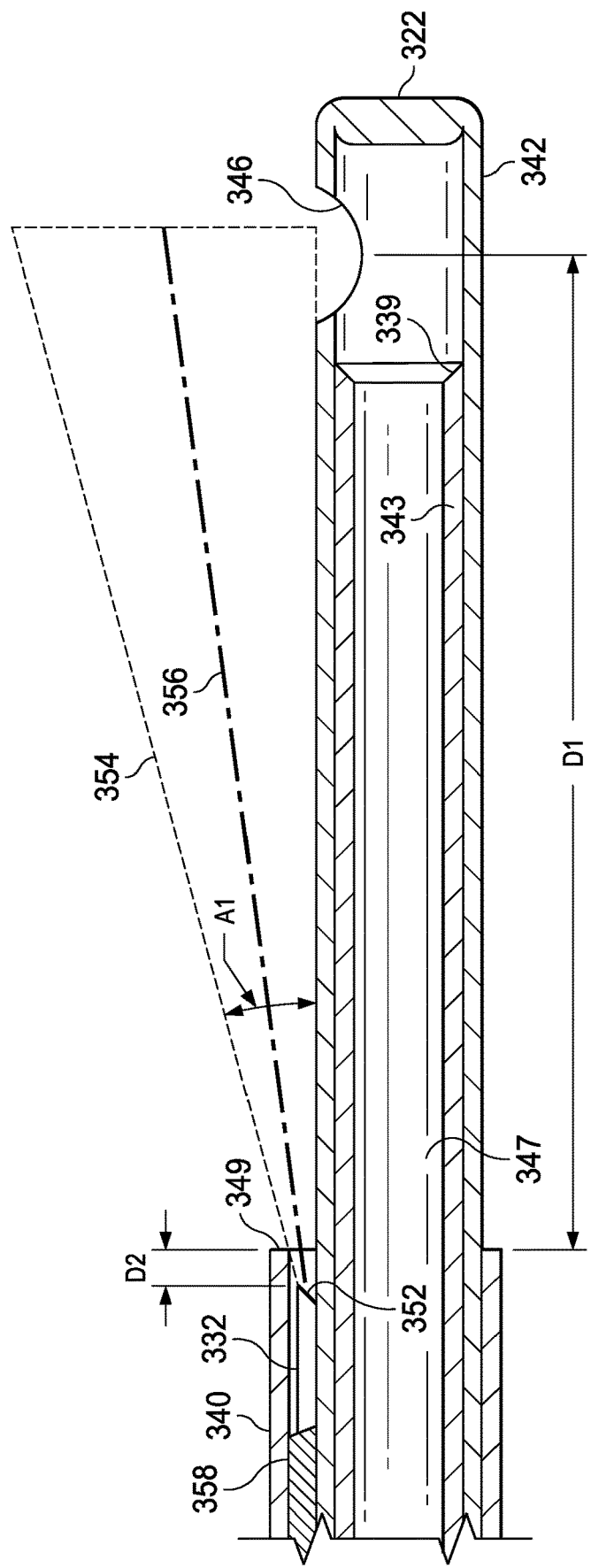
FIG. 5A is a cross-sectional illustration of the distal end of the exemplary surgical instrument in FIG. 3, according to aspects of the present disclosure.

FIG. 5A show therein a cross-sectional view of the distal region of the vitrectomy needle 320 of FIGS. 3A-C. The sheath 340 surrounds the elongate tubular member 342 and an inner tubular member 343, which is an elongate tubular member extending within a lumen 347 of the elongate tubular member 342. The distal edges 339 of the inner tubular member 343 may be sharpened or include a shape to facilitate cutting of vitreous as the inner tubular member 343 oscillates back and forth within the lumen 347 and cycles past the port 346. Vitreous aspirated into the port 346 may be cut by the oscillating inner tubular member 343.

Figure 5B:
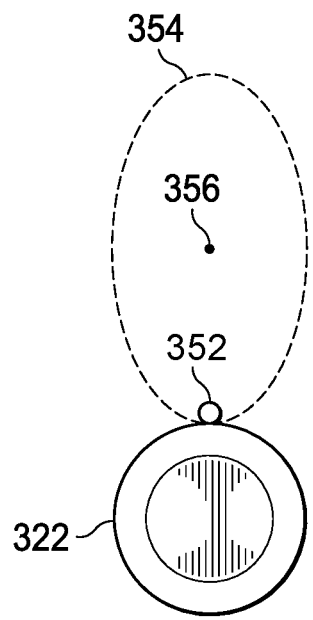
FIG. 5B is an end view of the distal end of the exemplary surgical instrument of FIG. 5A showing an illumination pattern thereof, according to aspects of the present disclosure.
Figure 5C:
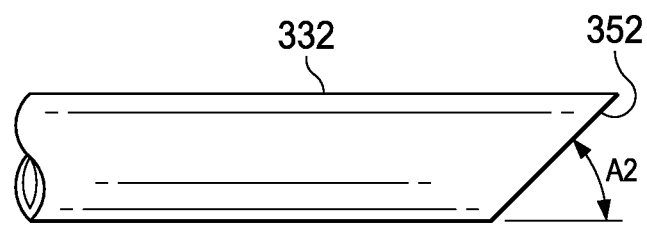
FIG. 5C is a detailed view of a distal end of an optical fiber that may be included in the exemplary surgical instrument of FIG. 5A, according to aspects of the present disclosure.

The sheath 340 further surrounds and encloses the optical fiber 332. A distal edge 349 of the sheath 340 may be offset from a center of the port 346 by a distance D1. The distance D1 may range from about 2 mm to about 3 mm in some implementations. Other implementations may have a distance D1 that is greater or lesser than this range. The optical fiber 332 includes a face 352 at the distal end thereof. Illumination in an illumination beam 354 may be emitted from the face 352 to illuminate an area proximate the port 346. For example, during a vitrectomy procedure, the illumination beam 354 may be generally ovoid in shape and centered at the central illumination point 356, as shown in FIG. 5B. As shown in FIG. 5A, the illumination beam 354 may span an angle A1 and may have a portion that is tangential to the outer surface of the elongate tubular member 342. In some implementations of the probe 300, the face 352 may be angled such that no portion of the illumination beam 354 contacts the outer surface of the elongate tubular member 342 at all. For example, FIG. 5C provides a detailed view of the distal end of the optical fiber 332 and the face 352 thereof. The face 352 may be a beveled face that forms an angle A2, which may range from about 20° to about 50°. In some implementations, the angle A2 is about 35°. Other angles are contemplated in other implementations.

To protect the face 352 at the distal end of the optical fiber 332, the distal end thereof may be offset from the distal edge 349 of the sheath 340 by a distance D2, as shown in FIG. 5A.

Implementations of the probe 300 may include a distance D2 ranging from about 10 μm (micrometers) to about 50 μm. In some implementations, the distance D2 may be about 25 μm. This distance D2 may provide sufficient protection of the optical fiber 332 and the face 352 and may also provide a limit to the angle A1 of the illumination beam 354 to control the light and better enable the surgeon to visualize tissue material proximate the distal tip 322, thereby aiding a surgeon in removing vitreous via the port 346. As shown in FIG. 5A, a central illumination point 356 may be angled away from the surface of the outer tubular member 342 to avoid glare being reflected off the exterior surface. In some implementations, some rays of the illumination beam may be incident upon the exterior of the outer tubular member 342.

The gap between the outer surface of the elongate tubular member 342 and the inner surface of the sheath 340 further includes a fill material 358 that covers a portion of the optical fiber 332. The fill material 358 may be an adhesive material that serves to secure the optical fiber 332 to the elongate tubular member 342 and/or the sheath 340. In some implementations, the fill material 358 may be a portion of the sealant material injected through the opening 348 in the sheath 340 as shown in FIG. 4B.

Figure 6A:
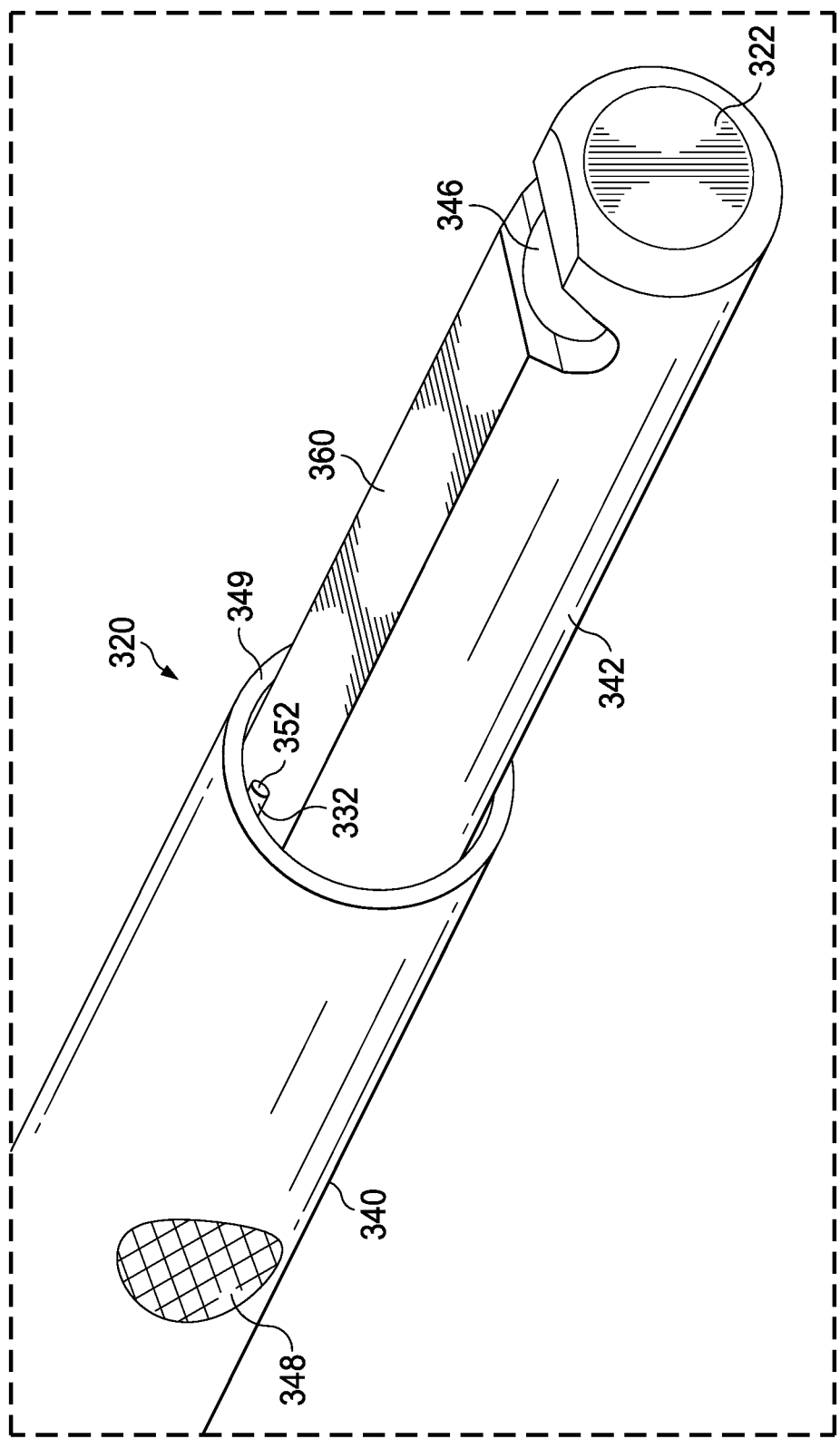
FIGS. 6A and 6B are detailed perspective views of the distal ends of exemplary surgical instruments, according to aspects of the present disclosure.
Figure 6B:
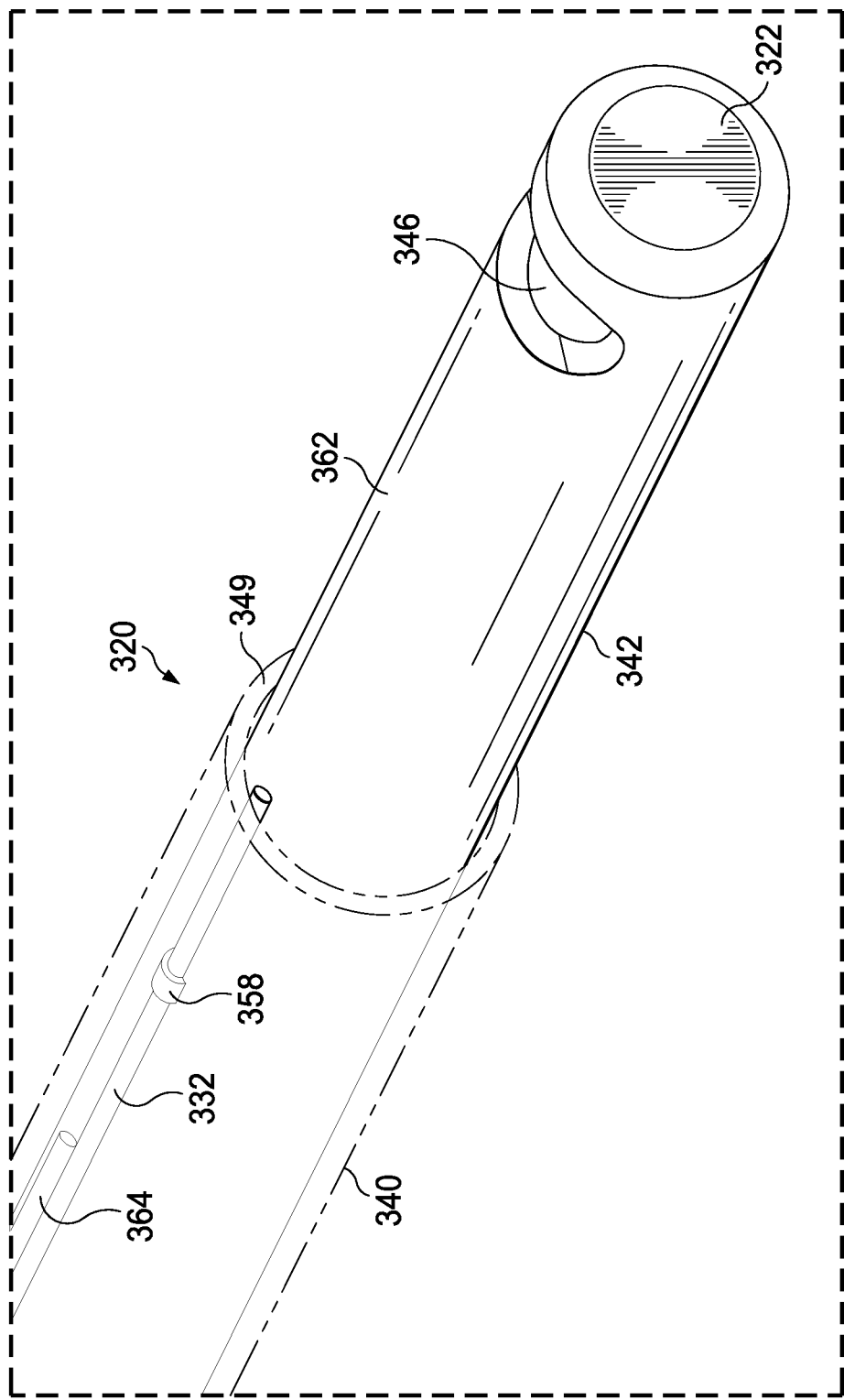

Referring now to FIGS. 6A and 6B, shown therein are implementations of the distal portion of the needle 320 of the probe 300. As shown in FIG. 6A, a sealant material is visible in the opening 348 in the sheath 340. The sealant material may seal off any gaps would otherwise be present between the elongate tubular member 342 and the sheath 340. FIG. 6A also depicts a flat surface 360 formed on the elongate tubular member 342. The flat surface 360 may provide a surface on which to secure the optical fiber 332. Further the flat surface 360 may be produced by removing material from the elongate tubular member 342 such that the thickness of the wall of the elongate tubular member 342 is smaller at the flat surface 360. This may facilitate inclusion of the optical fiber 332 while mitigating any increase in the diameter of the needle 320. Accordingly, the thickness of the wall removed to provide the flat surface 360 may correspond to the thickness of the optical fiber 332. Thus, in some exemplary implementations for a vitrectomy probe, about 20 μm to about 150 μm of thickness may be removed. In some implementations of the elongate tubular member 342, the lumen 347 extending therethrough may be offset away from the flat surface 360 to provide for a substantially uniform thickness of the wall at the flat surface 360 and of the wall of the elongate tubular member 342 opposite the flat surface 360. The flat surface 360 may be a planar surface, in some implementations.

FIG. 6B depicts an implementation of the needle 320 in which the outer surface of the elongate tubular member 342 is fully cylindrical, i.e. does not include the flat surface 360 shown in FIG. 6A. The implementation shown in FIG. 6B further depicts a patch of the fill material 358 securing the optical fiber 332 in position under the sheath 340. The depicted implementation also shows an elongate structure referred to as a fiber guard member 364, which extends along a length of the elongate tubular member 342. The fiber guard member 364 may prevent a compressive force applied by the sheath 340 from affecting the performance of the optical fiber 332 and may ensure that the optical fiber 332 remains aligned parallel to a central axis of the elongate tubular member 342, and may also ensure that the optical fiber 332 remains free to displace axially along and independently of a proximal region of the elongate tubular member 342, so as to reduce axial strain on the optical fiber 332 while permitting it to move independently into and out of the slack chamber 330. In some implementations, the optical fiber 332 may extend along the fiber guard member 364 for most of the length of the optical fiber 332. The fiber guard member 364 may be an elongate structure, or series of aligned structures, such as a wire made of metal or a polymeric material welded, adhered or otherwise joined to the outer surface of the elongate tubular member 342. Other implementations of the fiber guard member 364 may include a glass fiber or a line of rigidized or cured polymeric material, such as an adhesive. The thickness of the fiber guard member 364 may be greater than a diameter of the optical fiber 332, which may range from about 20 μm to about 150 μm, in various implementations. Accordingly, the thickness of the fiber guard member 364 may range from about 30 μm to about 200 μm, depending on the implementation. Naturally, some implementations of the needle 320 may include both the flat surface 360 and the fiber guard member 364. In some embodiments, a fiber guard member 364 that surrounds the optical fiber 332 may be provided to protect the optical fiber 332. For example, the fiber guard member 364 may be provided by a metallization layer around a length of the optical fiber 332. The metallization layer may provide structural rigidity to the metallized portion of the optical fiber 332. Other rigid polymers may be used rather than metal, in some embodiments. Embodiments of optical fiber 332 having such a protective coating or surrounding structure may have a diameter less than 200 μm or less than 50 μm, for example.

Figure 7A:
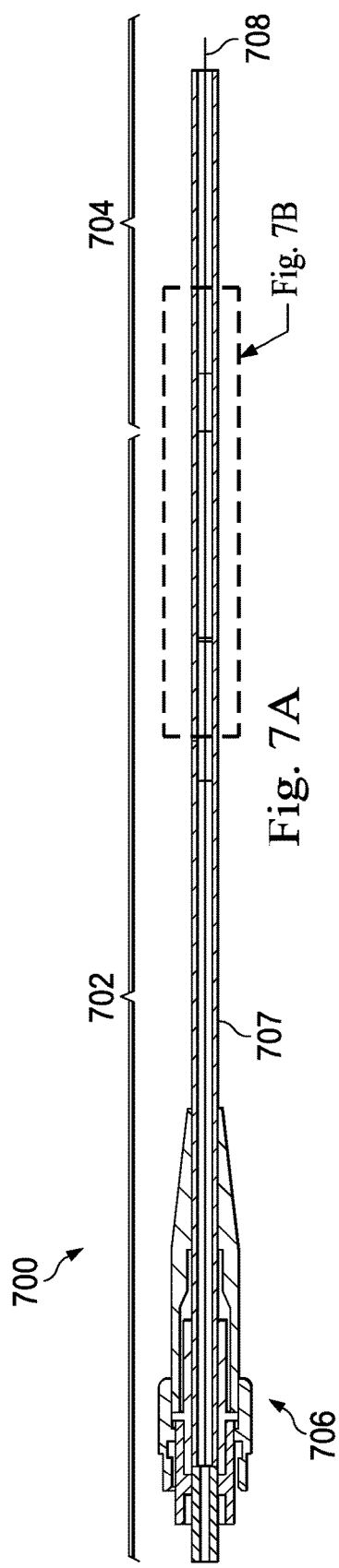
FIGS. 7A, 7B, and 7C depict cross-sectional views of an optical fiber that may be included in exemplary surgical instruments, according to aspects of the present disclosure.
Figure 7B:
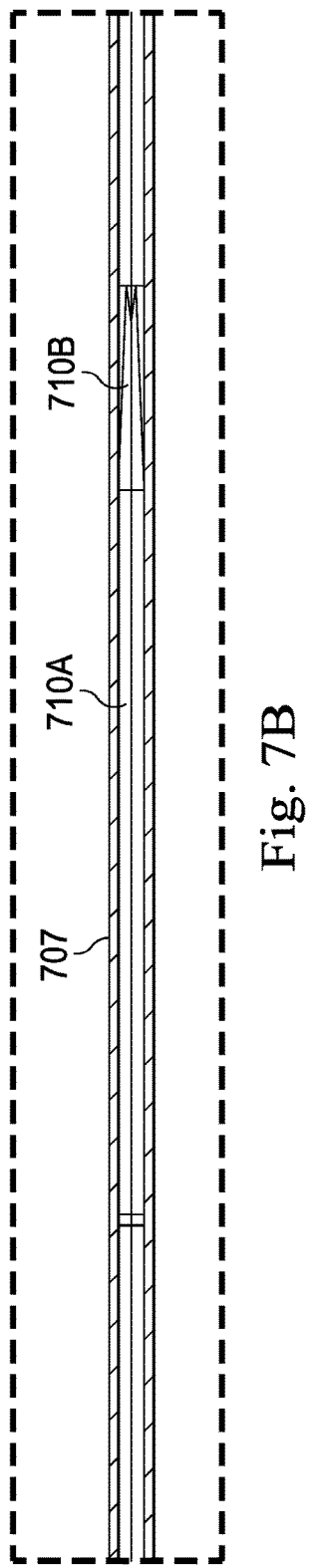
Figure 7C:
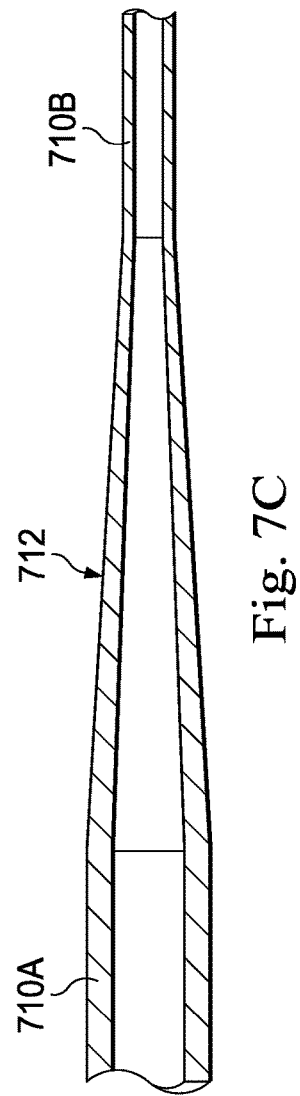

Referring now to FIGS. 7A, 7B, and 7C, shown therein are aspects of an optical fiber 700 which may be used in some implementations of the optical fiber 332. The optical fiber 700 may include a transmission assembly 702 and a distal assembly 704. The transmission assembly 702 may comprise about 80% or 90% of the total length of the optical fiber 700. For example, the transmission assembly 702 may be about 90 inches in length, while the distal assembly 704 may be about 10 inches in length. FIG. 7A depicts an optical fiber coupler 706 disposed at the proximal end of the optical fiber 700. The coupler 706 may secure the optical fiber 700 to the console 102 of FIG. 1 or to the fiber subsystem 120 contained therein. The coupler 706 may include an elongate portion that may prevent kinking close to the proximal end of the optical fiber 700. The optical fiber coupler 706 connects to a flexible outer member 707, which may be the first conduit 106 as shown in FIG. 1 and described herein. Accordingly, the flexible outer member 707 may contain and protect an optical fiber core 708.

FIG. 7B shows the optical fiber core 708 as a compound optical fiber core having multiple components axially aligned and joined to transmit light along the total length thereof. Some implementations of the optical fiber core 708 may include a first fiber portion 710A and a second fiber portion 710B. The fiber portions 710A and 710B may be formed from the same materials or from different materials. For example, the fiber portion 710A may be a silica or borosilicate fiber, while the fiber portion 710B may be a plastic fiber. In other implementations, the fiber portion 710A may be a plastic fiber, while the fiber portion 710B is a glass fiber. The fiber portion 710A and 710B may be glued or fused together.

As shown in FIG. 7C, the fiber portions 710A and 710B may be joined by a tapered optical fiber section 712 that has a proximal end with a first radius and a distal end with the second radius. The tapered optical fiber section 712 may join fiber portions of different diameters. In some implementations, the tapered optical fiber section 712 may be formed by heating the optical fiber core 708 and stretching the fiber. In some implementations, the tapered optical fiber section 712 may be about 20 mm in length, and may join an optical fiber portion 710A having a diameter of about 100 μm with an optical fiber portion 710B having a diameter of about 30 μm. These dimensions are exemplary only, and will vary depending on the implementation. In some implementations, a single, continuous optical fiber core extends the full length of the optical fiber 700.

As noted herein, some of the more specific implementations are described with respect to a vitrectomy probe in which an optical fiber provides for illumination of the vitreous at the distal tip of the vitrectomy probe. It should be noted that the described optical fiber may provide for other functions in other implementations. For example, the optical fiber included in implementations of the surgical instrument 110 may provide for transmission of laser light to provide a photocoagulation laser at a distal tip of the surgical instrument. Additionally, the surgical instrument 110 may be a non-surgical medical instrument in other implementations. For example, additional implementations may utilize the optical fiber in the performance of optical coherence tomography (OCT) imaging, rather than or in addition to any surgical functions performed by implementations of the medical instrument. Accordingly, such surgical instruments are included within the scope of the present disclosure.

Persons of ordinary skill in the art will appreciate that the implementations encompassed by the present disclosure are not limited to the particular exemplary implementations described above. In that regard, although illustrative implementations have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An illuminated microsurgical instrument system comprising:
    a microsurgical instrument having a distally projecting tubular member arranged to perform a medical procedure at an interventional site, the tubular member having a distal tip and an outer surface, the outer surface having a flat surface formed therein, wherein the flat surface is planar and is parallel to a longitudinal axis of the tubular member, and wherein a thickness of a wall of the tubular member is smaller at the flat surface;
    a sheath member surrounding a portion of the tubular member and extending toward the distal tip of the tubular member; and
    an optical fiber extending along a length of the flat surface between the tubular member and the sheath member within a space between an inner surface of the sheath member and the outer surface of the tubular member, wherein a tip of the optical fiber is directed toward the distal tip of the tubular member;
    wherein the sheath member and the optical fiber do not extend along an entire length of the tubular member.

2. The illuminated microsurgical instrument system of claim 1, wherein the optical fiber is fixed in position at least in part relative to the sheath member.

3. The illuminated microsurgical instrument system of claim 1, wherein a lumen extending within the tubular member is centered within the tubular member.

4. The illuminated microsurgical instrument system of claim 1, wherein a distal edge of the sheath member is disposed at a location closer to the distal tip of the tubular member than is the optical fiber, such that the optical fiber is recessed from the distal edge.

5. The illuminated microsurgical instrument system of claim 1, wherein the tip of the optical fiber is beveled at an angle toward the flat surface.

6. The illuminated microsurgical instrument system of claim 5, wherein the tip of the optical fiber causes a field of illumination to be directed substantially away from the flat surface.

7. An illuminated microsurgical instrument system comprising:
    a microsurgical instrument having a tubular member arranged to perform a medical procedure at an interventional site, the tubular member having a distal tip and an outer cylindrical surface;
    a sheath member surrounding a portion of the tubular member and extending toward the distal tip of the tubular member;
    an optical fiber extending along a length of the tubular member within a space between the outer cylindrical surface of the tubular member and an inner surface of the sheath member, wherein a tip of the optical fiber is recessed proximally from a distal edge of the tubular member; and
    an opening extending through a sidewall of the sheath member, the opening providing access to a volume defined by and between an inner wall of the sheath member and the outer cylindrical surface of the tubular member;
    wherein cured adhesive at least partially fills the volume defined by and between the inner wall and the outer cylindrical surface to provide a seal therebetween.

8. The illuminated microsurgical instrument system of claim 7, wherein the tip of the optical fiber is beveled toward the outer cylindrical surface of the tubular member.

9. The illuminated microsurgical instrument system of claim 8, wherein a face of the optical fiber forms an angle with respect to the outer cylindrical surface ranging from about 30 degrees to about 40 degrees.

10. The illuminated microsurgical instrument system of claim 7, further comprising a fiber guard member disposed along a length of the microsurgical instrument adjacent to the optical fiber, to protect the optical fiber from compressive forces between the outer cylindrical surface of the tubular member and the sheath member.

11. The illuminated microsurgical instrument system of claim 10, wherein the fiber guard member is a rigid structural member surrounding a length of the optical fiber.

12. The illuminate microsurgical instrument system of claim 10, wherein the fiber guard member is a metal wire, a glass fiber, or a line formed of rigidized polymeric material.

13. The illuminated microsurgical instrument system of claim 7, wherein the optical fiber comprises a proximal portion having a first diameter and a distal portion have a second diameter that is smaller than the first diameter.

14. An illuminated medical probe comprising:
    a handpiece housing configured to be held in a human hand, the handpiece housing including:
    a proximal end arranged to receive an optical fiber coupled to an illumination source,
    a distal end coupled by a collar structure to an elongate tubular member, the tubular member having a distal tip and an outer surface, the outer surface having a flat surface formed therein, wherein the flat surface is planar and is parallel to a longitudinal axis of the tubular member, and wherein a thickness of a wall of the tubular member is smaller at the flat surface, an optical fiber slack chamber disposed between the proximal end and the distal end; and an optical fiber extending within the optical fiber slack chamber and extending through the collar structure and along a portion of the elongate tubular member, wherein a distal region of the optical fiber is secured at a distal end thereof to the outer surface of the elongate tubular member along a length of the flat surface, the optical fiber being arranged to axially displace along the elongate tubular member and slideably transition through the collar structure between the elongate tubular member and a slack portion including one or more bends disposed within the optical fiber slack chamber;

wherein the optical fiber extends along a length of the flat surface between the tubular member and a sheath member within a space between an inner surface of the sheath member and the outer surface of the tubular member;

wherein the sheath member and the optical fiber do not extend along an entire length of the tubular member.

15. The illuminated medical probe of claim 14, wherein the elongate tubular member comprises an outer vitrectomy needle and an inner vitrectomy needle.

16. The illuminated medical probe of claim 14, wherein the optical fiber slack chamber is disposed in the handpiece housing, or in a flexible conduit coupled to the handpiece housing, or in an optical connector.

17. The illuminated medical probe of claim 14, wherein the optical fiber is secured, at least partially, to a cylindrical outer surface of the elongate tubular member relative to an elongate sheath member.

18. The illuminated medical probe of claim 14, wherein the optical fiber includes a tapered optical fiber section coupling a proximal fiber section having a first diameter to a distal fiber section having a second diameter that is smaller than the first diameter.

* * * * *